United States Patent [19]

Bromberg

[11] 4,055,768
[45] Oct. 25, 1977

[54] LIGHT MEASURING APPARATUS

[76] Inventor: Nathan S. Bromberg, 461 Conant Road, Weston, Mass. 02193

[21] Appl. No.: 721,065

[22] Filed: Sept. 7, 1976

[51] Int. Cl.$^2$ .............................................. G01N 21/38
[52] U.S. Cl. .................................. 250/461 R; 356/85
[58] Field of Search .................. 250/364, 458, 461 R, 250/461 B; 356/85

[56] References Cited

U.S. PATENT DOCUMENTS

| 3,684,377 | 8/1972 | Adams et al. | 250/461 B |
| 4,006,360 | 2/1977 | Mueller | 250/461 B |

Primary Examiner—Davis L. Willis
Attorney, Agent, or Firm—Wolf, Greenfield & Sacks

[57] ABSTRACT

Apparatus usable as a fluorometer for measuring the concentration of fluorescent material in a specimen employs a flashing lamp to illuminate the specimen with excitation radiation. The intensity of the fluorescence emitted by the specimen is therefore modulated at the flash rate. That modulated fluorescence is converted by a photodetector to an electrical signal. The electrical signal is amplified and is passed through a phase sensitive detector to an integrator. The phase sensitive detector is regulated to operate at a rate related to the flash rate whereby an appropriately rectified signal is fed to the integrator. When the specimen has been subjected to a selected amount of excitation radiation, a signal is generated which marks the end of the integration interval. The accumulated signal in the integrator is then measured to obtain a measurement of the quantity of fluorescent material in the specimen. The apparatus is also usable as a nephelometer to measure the light scattering properties of a specimen illuminated by the flashing lamp.

6 Claims, 17 Drawing Figures

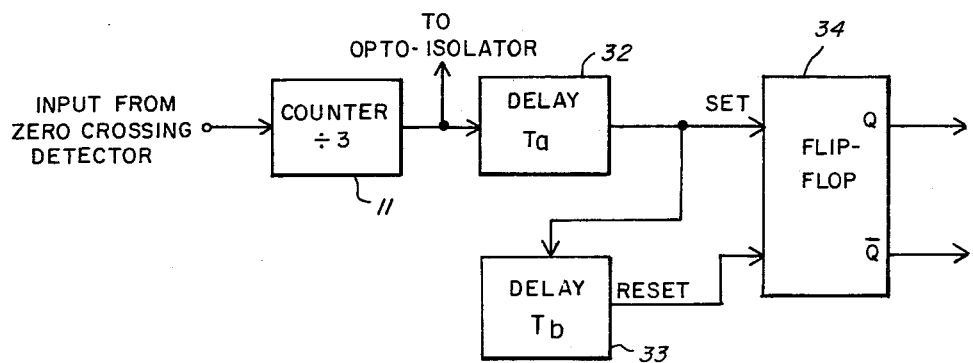
Fig. 7
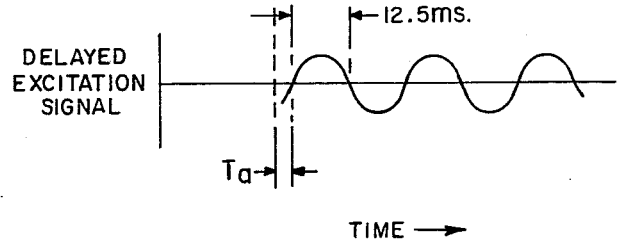
Fig. 8A
Fig. 8B
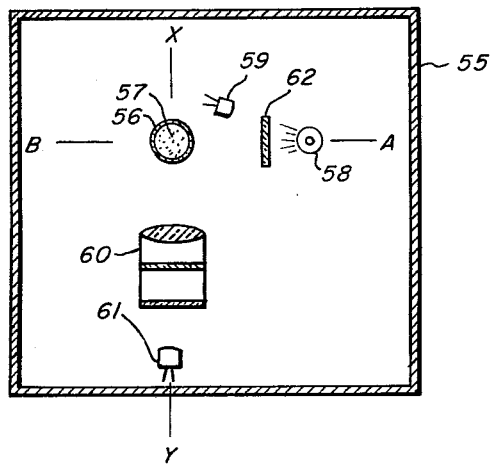
Fig. 9

4,055,768

LIGHT MEASURING APPARATUS

FIELD OF THE INVENTION

This invention relates in general to fluorometry and more particularly pertains to apparatus for measuring the emitted fluorescence of stimulated substances and converting the measurement to a digital display.

BACKGROUND OF THE INVENTION

Lead is known to be a toxic substance that interferes with the production of red blood cells in the human body. It has been determined that lead prevents the body from putting iron into hemoglobin in the red cell generation process occurring in the bone marrow. This lack of iron in the red blood cells permits zinc to take the place of the missing iron in the hemoglobin. Consequently the amount of zinc protoporphyrin, a product of the generation of hemoglobin, is a measure of lead poisoning of the body where the lack of iron in the red blood cells results from the injection of lead.

The presence of zinc protoporphyrin in the blood can be due to causes other than lead poisoning. For example, if the body has an insufficient intake or iron due to a poor or unbalanced diet, the body will be unable to supply the iron needed in the production of red blood cells and zinc will tend to take the place of the missing iron in the cells. As another example, where profuse or continual bleeding necessitates the replacement of lost blood, the production of new red blood cells may require more iron than the body has in reserve. Whatever the cause, the presence of zinc protoporphyrin indicates a malfunction in the generation of hemoglobin and a large amount of zinc protoporphyrin usually is a sign that medical treatment is needed.

Zinc protoporphyrin is a fluorescent substance and when exited by radiation in the band from about 415 nanometers (nm.) to 440 nm. in wavelength, fluoresces and emits light whose wavelength is in the range from 570 nm. to 660 nm. The peak emission of fluorescent light from zinc protoporphyrin occurs when the excitation radiation is at 424 nm. and when so excited the maximum fluorescent intensity occurs at 595 nm.

It has been proposed to measure the quantity of zinc protoporphyrin in a blood sample by fluorometry to provide a quick and easy method for detecting lead poisoning and obtaining a measure of its level in the body. However, the amount of zinc protoporphyrin in whole blood is never very large and because of its low concentration, its fluorescent intensity in a blood sample is very low. The amount of radiation emitted by zinc protoporphyrin is directly proportional to its concentration in the blood.

In the preferred mode of use of the invention for the detection of lead poisoning, fluorescence analysis is carried out directly without dilution of the blood sample and therefore the sample is excited by front face excitation illumination. For accurate results, the "front face" technique requires the sample to absorb all the excitation radiation. Further, by employing an excitation source that has minimal infrared and ultraviolet emission, chemical decomposition of the blood sample by the action of the radiant energy is largely avoided. Although not an essential feature of the invention, photolysis can be further inhibited by turning off the excitation source immediately after fluorometric analysis or dropping a mechanical shutter.

THE INVENTION

The invention resides in a fluorometer employing a modulated source of excitation radiation to illuminate the fluorescent specimen. In the fluorometer, an excitation channel monitors the radiation of the modulated excitation source and emits a signal when the specimen has been illuminated by a predetermined total amount K of radiant energy. The fluorescence of the specimen is simultaneously monitored by a fluorescence channel which measures the intensity of the fluorescence emission of the sample by converting that emission to an electrical signal. In the fluorescence channel, the fluorescence intensity signal is integrated by causing an electrical charge to accumulate in a capacitor. At the conclusion of the integration, which is determined by K signal, the capacitor is discharged at a controlled rate and the time for completion of discharge is converted to a count that is a measure of the concentration of the fluorescent material in the sample. The count is then displayed in digital form by a display device.

BRIEF DESCRIPTION OF THE DRAWINGS

FIG. 7 is a block diagram of the arrangement employed to generate signals to control the operation of the switches in the phase sensitive detector.

FIGS. 8A and 8B show the difference in phase between waveforms occurring in the operation of the invention.

FIG. 9 depicts an alternative optical arrangement for the invention.

DETAILED DESCRIPTION OF PREFERRED EMBODIMENT

The blood sample is placed on a transparent glass microscope cover slip and the slip is placed in an enclosure where it is subjected to radiation emitted by an excitation source. Ideally, the enclosure is lined with a non-reflective, non-fluorescent material. The excitation source is a lamp of the type having a tube internally coated with a fluorescent material excited by a gaseous (mercury) arc discharge occurring in the tube. The fluorescent coating in the tube is a narrow band phosphor selected to have its peak emission at 424 nm. Such lamps, preferably, are operated with alternating current (a.c.) to cause the direction of the arc discharge to be reversed from time to time to inhibit migration of the mercury and prevent the electrodes from building up deleterious deposits.

Figure 1:
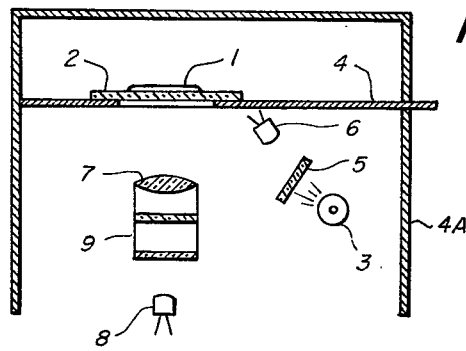
FIG. 1 schematically depicts the preferred optical arrangement employed in the invention.

As schematically depicted in FIG. 1, the blood specimen 1 on the glass slip 2 is exposed to radiation emitted from the excitation source 3. The fluorescent lamp 3 has an internal mirror coating that causes the light to be reflected toward an optical filter 5 which narrows the band of the excitation radiation that illuminates the blood specimen. Scattering of the incident radiation is minimized by the blood being flat against the smooth surface of the glass slip. A photodetector 6 is disposed to measure the intensity of the excitation radiation emerging from optical filter 5. The pass band of optical filter 5 is such as to block the transmission of radiation having a tendency to cause other materials in the blood specimen to fluoresce while transmitting those wavelengths that excite the zinc protoporphyrin to fluorescence. The fluorescent light emitted by the excited zinc protoporphyrin in the blood specimen passes through a condenser lens 7 that causes the viewed image of the blood specimen to appear upon a photodetector 8. The lens 7 is disposed so that it views the front face of the glass slip but is out of the path of excitation radiation reflected from the glass slip. Some of the excitation radiation that is incident on the glass slip and on the blood specimen is scattered and part of that scattered radiation passes through the lens 7. Consequently, an optical filter 9 is arranged to admit light that is in the band of fluorescent radiation emitted by zinc protoporphyrin and to reject or greatly attenuate radiation outside that band.

To prevent extraneous radiation from interfering with the operation of the fluorometer, the instrument is provided with a housing 4A that encloses the excitation source, the blood specimen, the optical filters and the photodetectors. The housing is provided with a sliding carriage 4 that permits the blood specimen to be inserted into the housing in a position where it is viewed by the lens 7 and is illuminated by the lamp 3. The sliding carriage can be arranged in any suitable manner to move the slip into and out of the housing through a slot in the housing's wall. The interior of the enclosure is lined or painted with a non-reflective, non-fluorescent material. Fluorescence from sources other than the blood sample will, if incident upon the photodetector 8, tend to affect the accuracy of the instrument. That spurious fluorescence, if it is sufficiently constant, can be compensated for by adjustment of the "zero" setting of the instrument.

Fluorescence intensity is a function of intrinsic factors such as quantum efficiency, absorbtivity, etc., which are constant for each fluorescent material, the extrinsic factors of intensity of excitation and concentration of fluorescent material in the sample, and a geometry factor which is a constant for each fluorometer. Expressed mathematically, $$f(t) = Q \times C \times e_x(t) \times G$$

where
 $f(t)$ is the fluorescence intensity
 $Q$ is the constant for the intrinsic factors
 $C$ is the concentration of emitter material
 $e_x(t)$ is the intensity of the excitation source
 $G$ is the geometry factor Fluctuations in the intensity of the lamp are taken into account by integrating the intensity of the excitation source over a period of time to obtain a known total radiated energy K. Further, random noise is rejected by the inherent narrow banding action of a phase sensitive detector. Accordingly, in the invention, K is chosen to insure that the excitation period extends over a sufficiently long interval to allow the noise rejection of the phase sensitive detector to occur. the equation $$K = \int_{t_o}^{t_1} e_x(t) \, dt$$

indicates that the source intensity is integrated until the integral equals K. Integrating $f(t)$, the fluorescence intensity, for the same time $t_1$ and then ending the integration results in the following $$F = \int_{t_o}^{t_1} f(t) \, dt$$

And since $$F = \int_{t_o}^{t_1} QCG \, e_x(t) \, dt$$

Then $$F = QCG \int_{t_o}^{t_1} e_x(t) \, dt$$

And $$F = (QGK) \, C$$

So that F is proportional to the concentration of the fluorescing substance.

Among the variables to be considered in quantitative analysis by fluorometry is the fluctuation in fluorescence caused by fluctuation in emission of the excitation source. To insure that the total amount K of excitation radiation is constant in each analysis of a blood specimen, the lamp is pulsed and the radiation is measured by the photodetector 6. In the preferred embodiment the lamp is pulsed at a 40Hz rate with alternating positive and negative sinusoidal signals obtained from the usual 60Hz supply mains. By so pulsing the lamp, the arc discharge is caused to alternate in direction to accord with the preferred mode of lamp operation. The manner of pulsing the lamp can be better understood from FIG. 2 which is a schematic block diagram of the preferred arrangement when that diagram is considered in conjunction with the waveforms depicted in FIGS. 3A to 3F.

Figure 2:
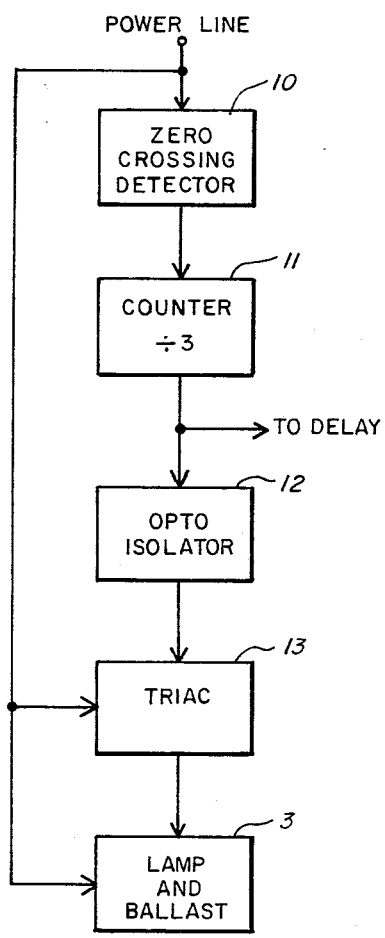
FIG. 2 is a block diagram showing the scheme employed in the invention for modulating the excitation source at a selected rate.
Figure 3A:
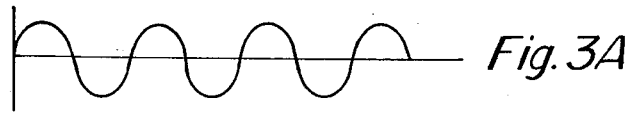
FIGS. 3A to 3F show certain of the waveforms occurring in the operation of the FIG. 2 arrangement.
Figure 3B:
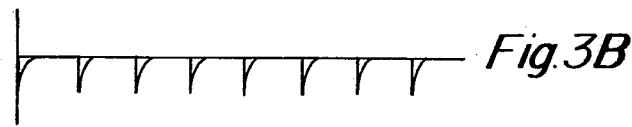
Figure 3C:
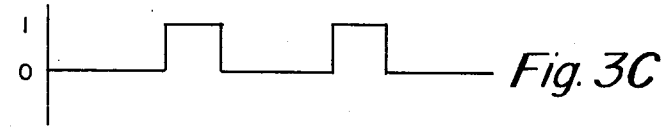
Figure 3D:
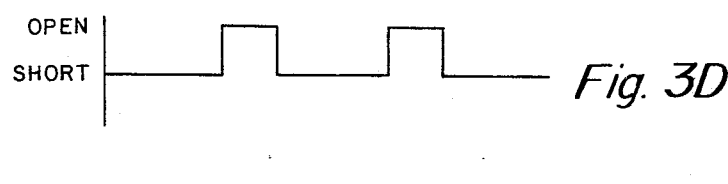
Figure 3E:
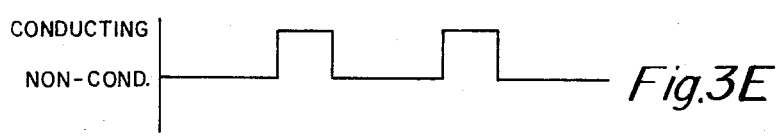
Figure 3F:
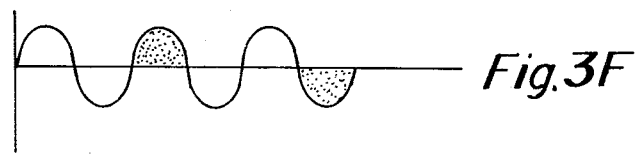

As shown in FIG. 2 the 60Hz power line provides an a.c. waveform of the kind depicted in FIG. 3A. The power line is coupled to a zero crossing detector 10 that emits a trigger signal each time the sinusoidal waveform crosses the zero axis, as indicated in FIG. 3B. The signal output of the zero crossing detector is fed to the input of a counter 11 which divides the count by three and emits a pulse, as shown in FIG. 3C, for every three signals fed into the counter. The counter 11 is of the logic type whose output remains at the logic 0 level until the the next input signal is received. Therefore, at every third input signal, the counter emits a pulse whose duration lasts until the next input signal is applied to the counter. The output of the counter is applied to the input of an opto-isolator 12. The opto-isolator is a device having a light emitter and a detector that are physically separated by a transparent insulator. The opto-isolator provides greatly improved electrical isolation while enabling the coupling of signals from one electrical circuit to another. The output of the opto-isolator is coupled to the gate of a triac 13 that controls the application of a.c. power to the lamp 3. During the times that the counter's output is at the 1 logic level, the opto-isolator's output is "open" as shown in FIG. 3D. The triac, as shown by the FIG. 3E waveform, conducts during the interval that the opto-isolator's output is "open." Consequently, power from the line is applied to the lamp during the conducting interval of the triac which is approximately one half cycle of the line frequency. The lamp, therefore, flashes at a 40Hz rate with the arc discharges alternating in direction as indicated in FIG. 3F by the stippled, half wave portions of the power line waveform which energize the lamp. Because the lamp is operated intermittently at a 40Hz rate, it is necessary to employ a ballast to insure the occurrence of an arc discharge in the lamp with each applied half wave of the a.c. power. The ballast facilitates maintaining the mercury in a condition conducive to the prompt formation of an arc discharge.

Figure 4:
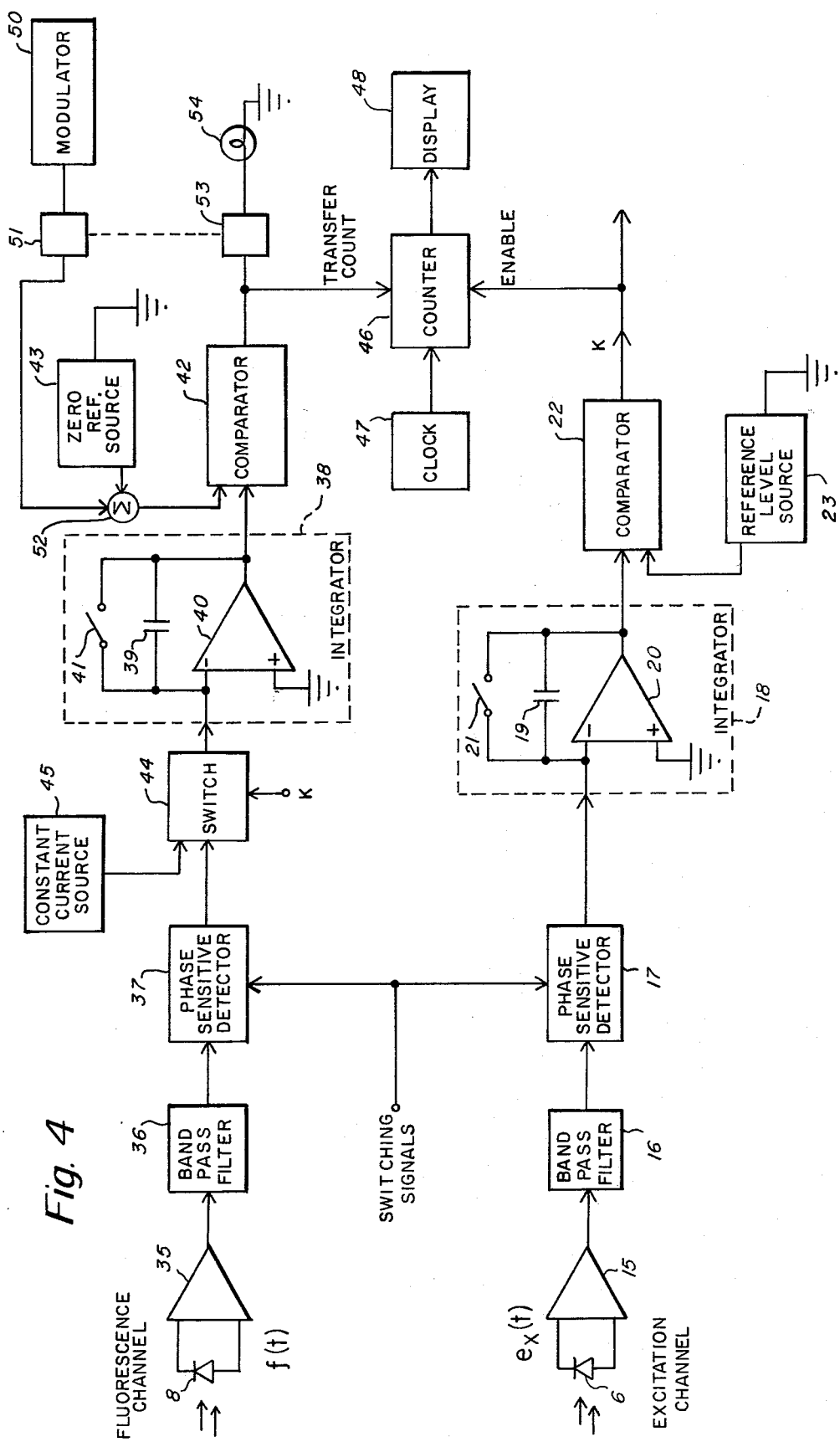
FIG. 4 schematically depicts the arrangement of signal channels employed in the preferred embodiment of the invention.

Turning now to FIG. 4, it can be seen that the invention utilizes two signal channels, each fed by its own photo-detector. The detector 6 in the "excitation" channel is arranged to receive radiation from the excitation source 3 after that radiation has passed through optical filter 5. The detector, preferably, is a solid state photodiode arranged so that its output is directly proportional to the intensity of the radiation that is incident upon it. The output of detector 6 is designated $e_x(t)$ in FIG. 4 to accord with the mathematical notation previously employed. The output of detector 6 is fed to an a.c. amplifier 15 whose output, in turn, is fed into a band pass filter 16 having its pass band centered on 40Hz. In practice, the band pass filter may be incorporated into the amplifier or may be distributed along the signal path and may therefore not exist as a distinct entity. The amplified signal is then applied to the input of a phase sensitive detector 17 which rectifies that signal in synchronism with signals derived from the output of counter 11. The rectified signal is integrated in an integrator 18 which may be of the conventional "Miller" type using a capacitor 19 in the feedback path of an operational amplifier 20. To reset the integrator to an initial condition, a switch 21 is arranged to short the plates of the capacitor 19 in response to a "reset" signal. Inasmuch as a practical switch has some resistance, the reset time preferably is at least 10 times the time constant formed by the switch's resistance and the capacity of the feedback capacitor. The output of the integrator is applied to a comparator 22 and is there compared with a fixed reference level provided by a reference level source 23. Upon reaching the fixed reference level, the comparator emits a signal indicating that the integrated light output of the excitation source has achieved the fixed level K.

Figure 5A:
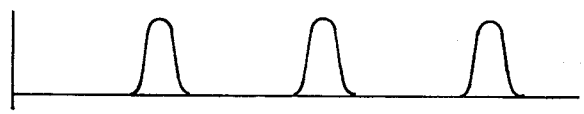
FIGS. 5A to 5C depict waveforms associated with the signal channels of FIG. 4.
Figure 5B:
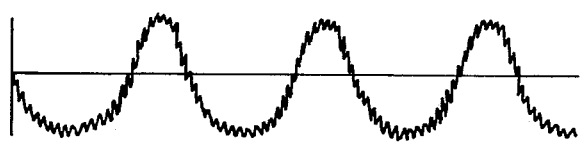
Figure 5C:
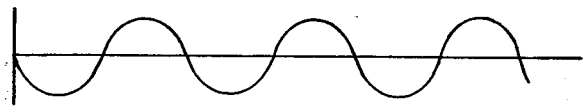

The input signal to amplifier 15 is a train of pulses, as indicated in FIG. 5A, occurring at the rate at which the lamp is flashed. Each pulse has a duration of approximately a half wave of the 60Hz power line frequency and occurs at each third half wave of the 60 cycle frequency. Inasmuch as there are 120 half waves in 60 a.c. cycles, the repetition rate is 40 pulses per second. In passing through a.c. amplifier 15, the pulsating signal loses its d.c. level and becomes an a.c. signal, as depicted in FIG. 5B. Filtering of the signal removes some of the noise and smooths out the signal so that it approximates the form shown in FIG. 5C. The signal is then applied to the input of the phase sensitive detector 17 which rectifies the signal and applies the rectified signal to the input of integrator 18.

Figure 6:
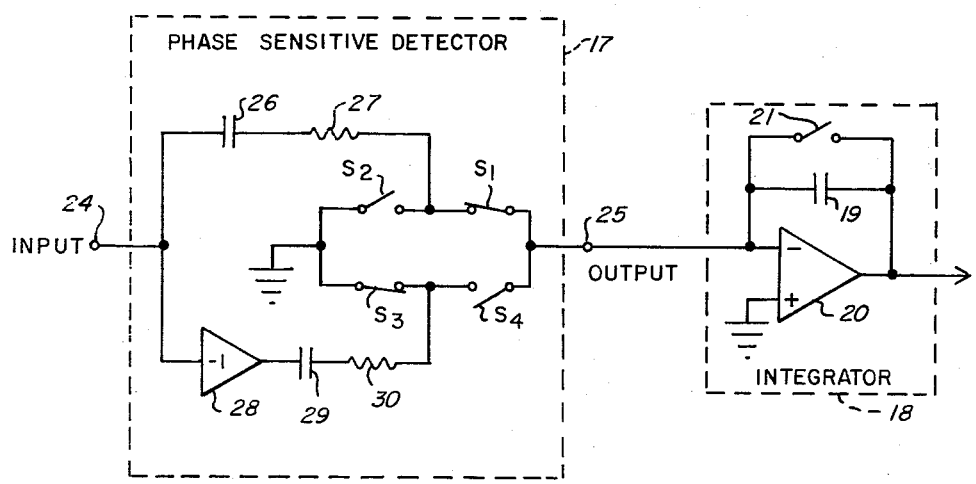
FIG. 6 is a schematic diagram showing details of the phase sensitive detector employed in the signal channels.

The phase sensitive detector is shown in detail in FIG. 6 where the signal input terminal is indicated at 24 and the output terminal is indicated at 25. The a.c. signal applied to the input terminal follows two paths to a set of switches arranged to alternately couple those paths to output terminal 25. The output terminal is maintained at "virtual" ground by the feedback of the operational amplifier 20 in integrator 18. In order that the signal applied at input terminal 24 shall see a relatively constant impedance, the signal paths in the phase sensitive detector 17 are grounded through the switches when not connected to the output terminal. Consequently, in each path, the signal sees either a "virtual" ground or a true ground.

In one path in the phase sensitive detector, the signal passes through a capacitor 26 in series with a resistor 27. In the other path, the signal is inverted by a unity gain amplifier 28 and then passes through capacitor 29 which is in series with resistor 30. In each path the capacitor and series resistor act as a high pass filter that blocks the passage of d.c. and attenuates the frequencies below the filter's cutoff. The d.c. component of any offset voltages from amplifier 28 or from the amplifier whose output is impressed at terminal 24 are blocked by capacitors 26 and 29.

When switch $S_1$ is closed to connect the signal to the input of integrator 18 switch $S_3$ is simultaneously closed to ground the signal emitted by inverter 28 while switches $S_2$ and $S_4$ are opened. At the appropriate time, switches $S_1$ and $S_3$ open and switches $S_2$ and $S_4$ close. The output signal from inverter 28 is then coupled through capacitor 29 and resistor 30 to the input of integrator 18 for the time that switches $S_4$ and $S_2$ are closed. The signal paths through the two high pass filters, consequently, terminate in either a virtual ground or a true ground. In the operation of the switches, capacitors 26 and 29 are not permitted to float.

The signals controlling switches $S_1$, $S_2$, $S_3$ and $S_4$ of the phase sensitive detector are derived from counter 11, as shown in FIG. 7, through a pair of delay devices 32 and 33 whose outputs control a flip-flop 34. Reverting to the excitation channel depicted in FIG. 4, it can be appreciated that the signal reaching the output of the phase sensitive detector 17 is delayed in phase relative to the output signal (FIG. 3C) of counter 11. The phase delay is due in part to the lag in the flashing of the lamp and in part to the transmission of the signal through the channel. Turning to FIG. 8A which shows the output signal of the counter 11 and to FIG. 8B which shows a component of the excitation signal that is applied through capacitor 26 and resistor 27 to switches $S_1$ and $S_2$, it is evident that the uninverted waveform of FIG. 8B is delayed in phase by time $T_a$ relative to the leading edge of the rectangular pulses in FIG. 8A. The FIG. 8B waveform is the ideal sinusoidal 40Hz component of the excitation signal. The 40Hz component of the excitation signal applied to switches $S_3$ and $S_4$ is essentially the same as depicted in FIG. 8B except that the waveform is inverted by the action of inverter 28. To cause switches $S_1$, $S_2$, $S_3$, and $S_4$ to operate properly, the switches are made to operate in synchronism with the zero axis crossings of the 40Hz component. To achieve that result, the output of counter 11 is coupled to delay device 32. That device preferably is a monostable multivibrator arranged to be triggered by the leading edge of the FIG. 8A pulses. Delay device 32 emits a "set" signal to flip-flop 34 at the end of delay interval $T_a$. That set signal also triggers a monostable multivibrator 33 which emits a "reset" signal to flip-flop 34 after an interval $T_b$ of 12.5 milliseconds. That interval is exactly the duration of a half cycle of the 40 Hz sinusoid. The complementary outputs Q and $\bar{Q}$ of flip-flop 34 control the opening and closing of switches $S_1$, $S_2$, $S_3$, and $S_4$ of the phase sensitive detector. Those switches are alternately opened and closed at the 40Hz rate in synchronism with the alternations of the 40Hz component of the signal applied to the phase sensitive detector.

In the fluorescence signal channel shown in FIG. 4, detector 8 is preferably a solid state photodiode arranged so that its current output is directly proportional to the intensity of fluorescent radiation incident upon it. In accordance with the mathematical notation previously adopted, the output of photodetector 8 is designated $f(t)$ in FIG. 4. Inasmuch as the fluorescence emitted by the zinc protoporphyrin in the blood sample is weak, the output of the photodetector 8 is coupled to an a.c. amplifier 35 having several stages of amplification. The amplified signal is filtered by a band pass filter 36 which may be part of amplifier 35 or may be distributed along the signal path. The pass band of the filter is centered at 40Hz which is the frequency at which the excitation source is pulsed. The amplified filtered signal is then applied to the input of the phase sensitive detector 37. That detector is identical to the detector 17 in the excitation channel and because the signal delay in both channels are the same, the switches in both those detectors are controlled by the switching signals emitted by flip-flop 34 (FIG. 7). The output of phase sensitive detector 37 is applied to the input of an integrator 38 having a capacitor 39 in the feedback path of operational amplifier 40. The integrator 38 is preferably arranged to be reset by a switch 41 in the same manner as previously described in connection with the resetting of integrator 18.

During the interval from $t_o$ to $t_1$, the rectified output signal of detector 37 is integrated by the integrator 38. When comparator 22 in the excitation channel emits a signal indicating that the constant K has been attained, the flashing of the lamp stops and a switch 44 is closed to connect a constant current source 45 to the input of integrator 38. It has been found that the output of the lamp is more stable if the lamp is left on. Consequently, rather than turn the lamp off, a shutter can be placed in front of the lamp to cut off excitation radiation to the sample upon the occurrence of the K signal or in lieu of turning off the lamp, switches $S_1$ and $S_4$ can both be placed in the "open" condition and switches $S_2$ and $S_3$ can both be closed upon the occurrence of the K signal. With switches $S_1$ and $S_4$ both open and switch 44 closed, the constant current source applies a signal whose polarity is opposite to the polarity of the signal accumulated in the integrator. Consequently, the integrator commences to integrate in the reverse direction and causes feedback capacitor 39 to discharge at a constant rate. At the time that comparator 22 closes switch 44, the output of that comparator simultaneously enables a counter 46 to begin counting the pulses emitted by a clock 47. The output of integrator 38 is coupled to a comparator 42 in the fluorescence channel which emits an output signal when the integrator's output drops to a "zero" reference level set by a source 43. The output of comparator 42 thereupon causes the count in counter 46 to be transfered to a display 48 which indicates the count in digital form as the concentration of zinc protoporphyrin.

To enable the apparatus to be properly calibrated, the constant current source 45 is adjustable to permit the current supplied by it to be set at a proper value when a specimen of a known concentration of zinc protoporphyrin is employed. To set the "zero" reference level in the fluorescence channel, a non-fluorescing specimen is used and the zero reference source 43 is adjusted to give a zero reading. Because the counter does not give readings below zero, the setting of the zero reference level tends to be inexact. To remedy that difficulty, when the zero reference adjustment is made, ganged switches 51 and 53 are closed. Closure of switch 53 connects a lamp 54 to the output of comparator 42. Closure of switch 51 connects the output of a modulator 50 to a summing junction 52. The modulator 50 emits a 10signal of very low amplitude which is combined at junction 52 with the output of reference source 43. The signal from junction 52 is applied as an input to comparator 42. When the reference source 43 is properly set, comparator 42 is activated at the 10 Hz rate and the lamp 54 flickers. If the reference source is set above the correct setting, the lamp remains on whereas if the source is below the correct setting the lamp is off. Consequently, adjustment of the zero setting is made simple by the depicted arrangement. When the zero setting has been made, switches 51 and 53 are opened to prevent the output of modulator 50 from affecting the measurement.

The invention is also useful for right angle fluorometry and for nephelometry. The top plan view of an optical arrangement for right angle fluorometry is schematically shown in FIG. 9 where the specimen is in a dilute solution 57 in a glass tube 56 situated in a housing 55. The light from the excitation source 58 which illuminates the specimen is directed along the A-B axis and the condenser lens in optics 60 is situated on the X-Y axis which is perpendicular to the A-B axis. In the FIG. 9 arrangement, photodetector 59 is arranged to respond to the intensity of the radiation emerging from optical filter 62. The light passing through optical filter 62 excites the fluorescent material in the tube and causes that material to fluoresce. The excitation radiation passing through the test tube is absorbed by the interior walls of housing 55 which is coated with a non-fluorescing material that does not reflect the incident light. The fluorescence emitted substantially along the X-Y axis is collected by the condenser lens in optics 60 and is passed through optical filters, as previously described in connection with FIG. 1, to a photodetector 61.

When used for nephelometry, the light from source 58 is scattered by the specimen. The scattered light collected by the condenser lens is then directed onto the photodetector 61. For nephelometry, the optical filters used in fluorescence analysis are not employed.

The invention can be used to measure light reflected from a specimen by positioning the optics 60 at the appropriate angle of reflection relative to the source of illumination.

Although the invention has been described as pulsing The lamp at a 40Hz rate when the power line frequency is 60Hz, other pulse rates which minimize interference from the power line can be used. An important consideration in selecting a suitable pulse rate is that the half wave pulses in the pulse train should alternately be of positive and negative polarity. The alternating polarity of the pulses tends to cause the interference which they induce in the detection circuits to be averaged out. Instead of using every third half cycle, as in FIG. 3F, the lamp can be pulsed with every fifth half cycle, every seventh half cycle, every ninth half cycle, etc.; that is, any odd number of half cycles is a suitable rate for the reduction of interference from the power line. Of course, the higher the odd number, the longer will be the period required to achieve the K amount of excitation radiation and the more stringent will be the requirement for retaining the charge in the integrator without loss during the interval between lamp flashes.

I claim:

1. Apparatus of the type for measuring light emitted, scattered, or reflected from a specimen, the apparatus comprising
   a. a source of excitation radiation arranged to illuminate the specimen,
   b. modulating means for modulating the excitation radiation,
   c. means for emitting a K signal when the specimen has been subjected to a selected amount of excitation radiation,
   d. a photodetector arranged to provide an electrical signal in response to the intensity of the light emitted, scattered, or reflected by the specimen,
   e. means for amplifying the output signal of the photodetector,
   f. a phase sensitive detector having the amplified signal applied to its input,
   g. means coupled to the modulating means and deriving signals therefrom which regulate the operation of the phase sensitive detector,
   h. an integrator having its input coupled to the output of the phase sensitive detector, and
   i. means responsive to the K signal for measuring the quantum of the signal accumulated in the integrator at the emission of the K signal.

2. Apparatus according to claim 1 wherein
   A. the source of excitation radiation is arranged to be intermittently energized by a.c. electrical power to produce excitation radiation, and
   B. the modulating means is arranged to cause half cycles of the a.c. electrical power which are alternately of different polarity to energize the excitation radiation source and the interval between successive half cycles is at least two half cycles in duration.

3. Apparatus according to claim 1, wherein the means responsive to the K signal includes
   1. a source of constant current,
   2. a switch for connecting the constant current source to the input of the integrator in response to the reception of the K signal,
   3. a comparator connected to the output of the integrator for emitting a signal when the output of the integrator reaches a zero reference level, and
   4. clock means for measuring the interval of time required for the constant current source to cause the output of the integrator to reach the zero reference level.

4. Apparatus according to claim 3 further including means for setting the apparatus to a zero datum comprising
   a. a source of electrical potential for supplying the zero reference level to an input of the comparator,
   b. a modulator for modulating the zero reference level signal applied to the input of the comparator, and
   c. means coupled to the output of the comparator for indicating activation of the comparator at the modulation rate, and for indicating settings above or below the modulated zero reference level.

5. Apparatus according to claim 1 wherein the means for emitting a K signal when the specimen has been subjected to a selected amount of excitation radiation includes
   1. a second photodetector arranged to supply an electrical signal in response to the intensity of the excitation radiation emitted by the source
   2. a second phase sensitive detector deriving its input from the output of the second photodetector
   3. a second integrator having its input fed by the output of the phase sensitive detector, and
   4. a second comparator coupled to the output of the second integrator, the second comparator emitting the K signal upon the output of the second integrator attaining a reference level.

6. Apparatus according to claim 5 wherein the second phase sensitive detector is regulated by the same control signals that regulate the operation of the first mentioned phase sensitive detector.

* * * * *